(12) United States Patent
Kraemer et al.

(10) Patent No.: US 8,430,891 B2
(45) Date of Patent: Apr. 30, 2013

(54) TRANSESOPHAGEAL GASTRIC REDUCTION DEVICE, SYSTEM AND METHOD

(75) Inventors: Stefan J. M. Kraemer, Seattle, WA (US); John M. Adams, Sammamish, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 0 days.

(21) Appl. No.: 13/069,992

(22) Filed: Mar. 23, 2011

(65) Prior Publication Data

US 2011/0172685 A1 Jul. 14, 2011

Related U.S. Application Data

(63) Continuation of application No. 10/686,427, filed on Oct. 14, 2003, now abandoned.

(51) Int. Cl.
*A61B 17/12* (2006.01)
(52) U.S. Cl.
USPC .......................................................... 606/142

(58) Field of Classification Search ................... 606/191, 606/192, 196, 197, 198, 142; 623/23.64, 623/23.65
See application file for complete search history.

(56) References Cited

U.S. PATENT DOCUMENTS

| 5,549,621 | A | * | 8/1996 | Bessler et al. | 606/151 |
| 6,558,400 | B2 | * | 5/2003 | Deem et al. | 606/151 |
| 2004/0148034 | A1 | * | 7/2004 | Kagan et al. | 623/23.65 |
| 2005/0247320 | A1 | * | 11/2005 | Stack et al. | 128/898 |

* cited by examiner

*Primary Examiner* — Ryan Severson
(74) *Attorney, Agent, or Firm* — Jens E. Hoekendijk

(57) ABSTRACT

A gastric reduction system and method provides for transesophageal formation of a gastric reduction pouch of the stomach. The system includes an expandable structure, which may be placed in a stomach and expanded to occupy a fractional volume of the stomach. An evacuator is then fed through the expandable structure and utilized to deflate the stomach and draw the stomach to and around the expandable structure to form the gastric reduction pouch. A self-deploying fastener is then deployed to maintain the gastric reduction pouch.

13 Claims, 5 Drawing Sheets

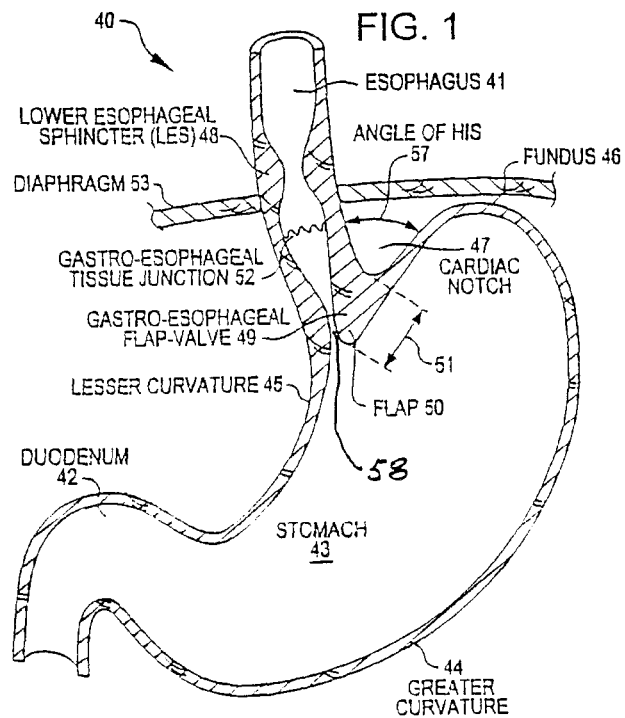
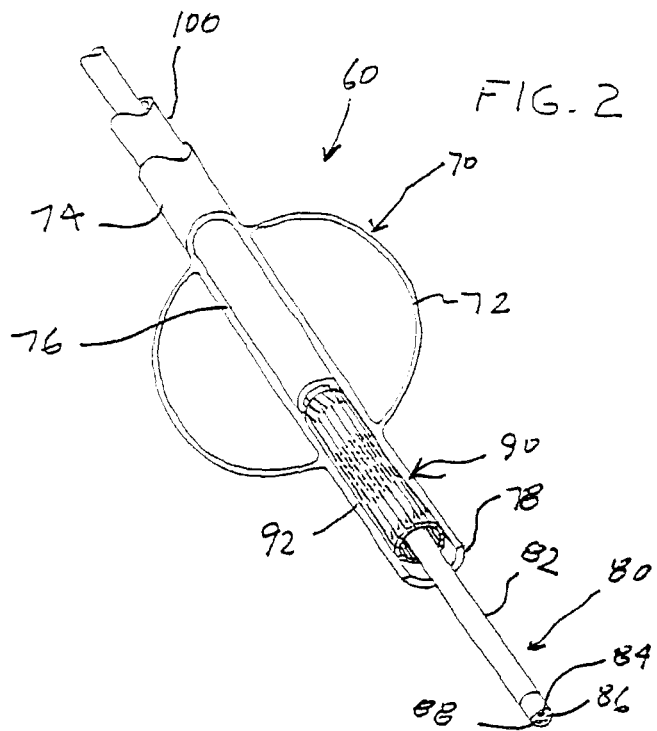

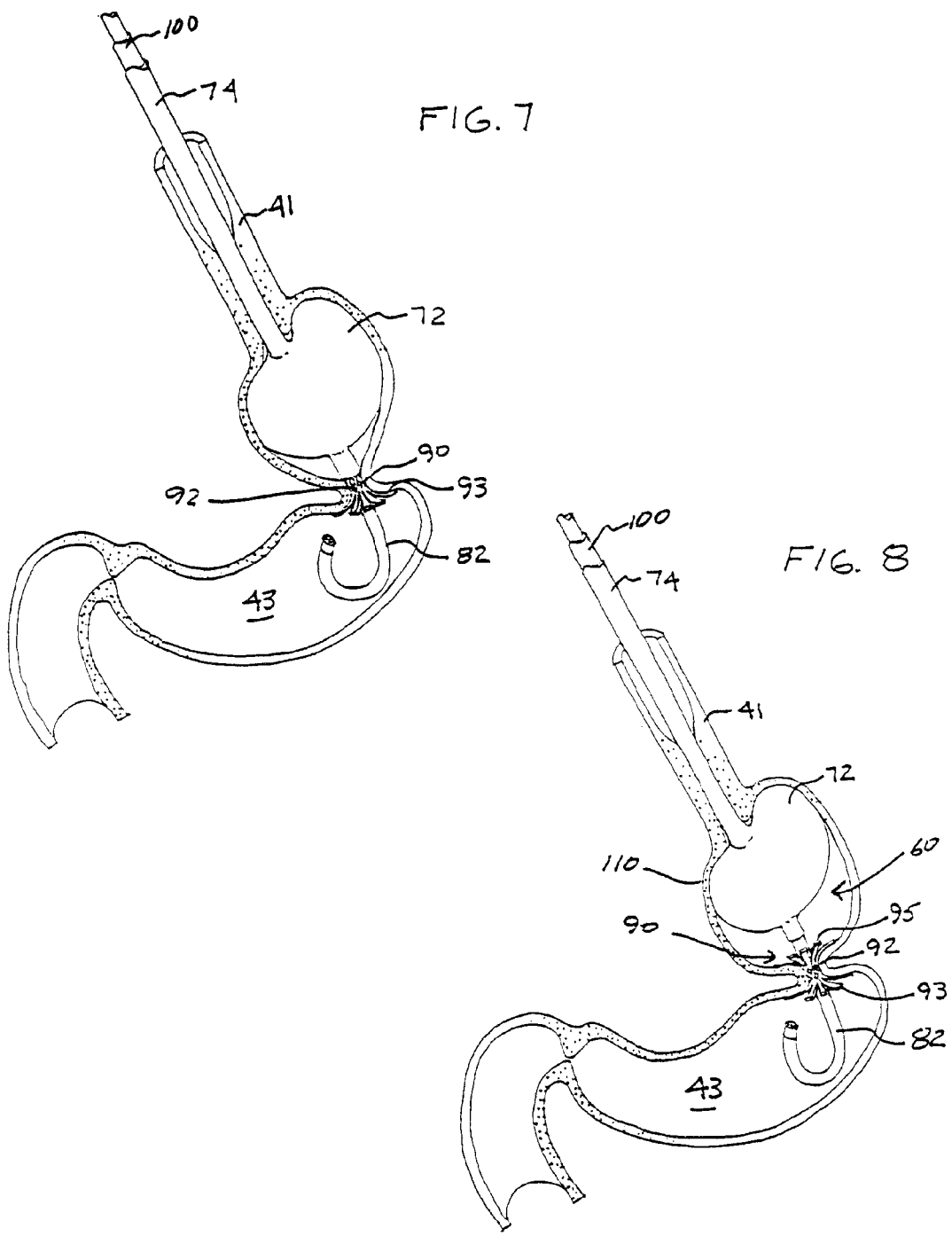

TRANSESOPHAGEAL GASTRIC REDUCTION DEVICE, SYSTEM AND METHOD

This application is a continuation application of application Ser. No. 10/686,427, filed on Oct. 14, 2003 now abandoned. The entire disclosure of which is hereby incorporated by reference for all purposes.

FIELD OF THE INVENTION

The present invention is generally directed to a therapy for treating obesity. The present invention is more particularly directed to a transesophageal gastric reduction device, system, and method for performing gastric reduction surgery while minimizing surgical invasion.

BACKGROUND OF THE INVENTION

Obesity is a complex chronic disease involving environment, genetic, physiologic, metabolic, behavioral and psychological components. It is the second leading cause of preventable death in the United States.

Obesity affects nearly one-third of the adult American population (approximately 60 million). The number of overweight and obese Americans has continued to increase since 1960. The trend is not slowing down. Today, 64.5% of adult Americans are categorized as being overweight or obese. Each year, obesity causes at least 300,000 excess deaths in the United States, and healthcare costs of American adults with obesity amounted to approximately $100,000,000,000 (100 billion dollars).

Obesity is not limited to the United States but is increasing worldwide. It is increasing worldwide in both developing and developed countries and is thought to be caused by environmental and behavioral changes resulting from economic development, modernization, and urbanization. Obesity is increasing in children as well. It is believed that the true health consequences of obesity have not yet become totally apparent.

Obesity is currently treated by dietary therapy, physical activity, behavioral therapy, drug therapy, and combinations thereof. Dietary therapy involves instruction on how to adjust a diet to reduce the number of calories eaten. Physical activity strategies include use of aerobic exercise, brisk walking, jogging, cycling, and swimming. Behavioral therapy involves changing diet and physical activity patterns and habits to new behaviors that promote weight loss. Drug therapy is most often used only in conjunction with appropriate lifestyle modifications.

One last treatment for obesity is surgery. Surgery is a treatment option which is generally reserved for persons with severe obesity and those who are morbidly obese. In addition, surgery is not generally performed until other methods of weight loss have been attempted and have been found to be ineffective. Persons who are severely obese are generally unable to physically perform routine daily activities, whether work-related or family functions and have a severely impaired quality of life due to the severity of their obesity.

Most obesity surgeries involve making changes to the stomach and/or small intestines. Currently, there are two types of obesity surgery: (1) restrictive; and (2) combined restrictive and malabsorptive. Operative procedures have been developed for each type of surgery. Each type of surgery has its own risks and side effects.

In restrictive surgery, bands or staples are used to create food intake restriction. The bands or staples are surgically placed near the top of the stomach to section off a portion that is often called a stomach pouch. A small outlet, about the size of a pencil eraser, is left at the bottom of the stomach pouch. Since the outlet is small, food stays in the pouch longer and the feeling of fullness lasts for a longer time. Current operative procedures for restrictive surgery include vertical banded gastroplasty, gastric banding, and laparoscopic gastric banding. In vertical banded gastroplasty, a stomach pouch is surgically created. In gastric banding, a band is used to create the stomach pouch. In laparoscopic gastric banding, a less invasive procedure, smaller incisions are made to apply the band. The band is inflatable and may be adjusted over time.

Each of the foregoing therapies for severe obesity has its risks and side effects. Each is invasive surgery and hence exhibits the risks commonly associated with all surgical procedures. Complications may include leaking of stomach juices into the abdomen, injury to the spleen, band slippage, erosion of the band, breakdown of the staple line, and stomach pouch stretching from overeating.

However, reductive surgery has proven successful. About 80% of patients lose some weight and 30% reach a normal weight. Hence, the benefits of gastric reduction surgery are generally believed to outweigh the attendant risks and potential complications.

The present invention is directed to an alternative device, system, and method for achieving gastric reduction. As will be seen hereinafter, the device, system, and method do not require surgical incisions and is thus less invasive than previous reduction therapies.

SUMMARY OF THE INVENTION

The invention generally provides a gastric reduction device comprising an expandable structure placeable in a stomach which, when expanded, occupies a portion of the stomach and an evacuator that deflates the stomach around the expandable structure to form a gastric reduction pouch. The expandable structure is preferably placeable in the stomach immediately adjacent and distal to an esophageal orifice associated with the stomach.

The expandable structure may comprise a balloon. The evacuator may extend distally from the expandable member and terminate within the stomach.

The device may further comprise a fastener that maintains the gastric reduction pouch. The fastener is preferably arranged to inwardly fold stomach tissue to fasten serosa tissue to serosa tissue of the stomach. The fastener may comprise a cylindrically shaped member having opposed ends and tissue engaging arms radially extending from each of the opposed ends.

The device may further comprise an endoscope that extends through the expandable member. The expandable member preferably forms a spherically shaped ring when expanded. The spherically shaped ring may include an axial passageway permitting the evacuator to extend through the passageway.

The present invention still further provides a gastric reduction system comprising an expandable structure, placeable in a stomach, and, when expanded, occupying a fractional volume of the stomach. The system further includes an evacuator that deflates the stomach and draws the stomach to and around the expandable member to form a gastric reduction pouch with stomach tissue and a fastener that is operable to maintain the gastric reduction pouch. The fastener may be carried by the evacuator.

The present invention still further provides a method comprising the steps of positioning an expandable structure in a stomach of a patient, expanding the expandable structure to occupy a portion of the stomach, and drawing the stomach around the expandable structure to form a gastric reduction pouch. The positioning step may include placing the expandable structure immediately distal to an esophageal orifice associated with the stomach. The expandable structure may comprise a balloon and the expanding step may include inflating the balloon.

The deflating step may include evacuating the stomach. To this end, an evacuator may be fed into the stomach. The evacuator may be fed into the stomach through the expandable structure.

The method may further include the step of maintaining the gastric reduction pouch. Maintaining the gastric reduction pouch may include inwardly folding stomach tissue to contact serosa tissue to serosa tissue to form a stoma. The inwardly folded stomach tissue may be fastened together.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 1 is a front cross-sectional view of the esophageal-gastro-intestinal tract from a lower portion of the esophagus to the duodenum;

FIG. 2 is a perspective view with portions cut away of a device embodying the present invention;

FIG. 7 is a cross-sectional view similar to FIG. 5 of the device delivering a fastener in a still further stage of the therapy;

FIG. 8 is a cross-sectional view similar to FIG. 5 of the device and fastener in a final stage of the therapy.

DETAILED DESCRIPTION OF THE INVENTION

Figure 3:
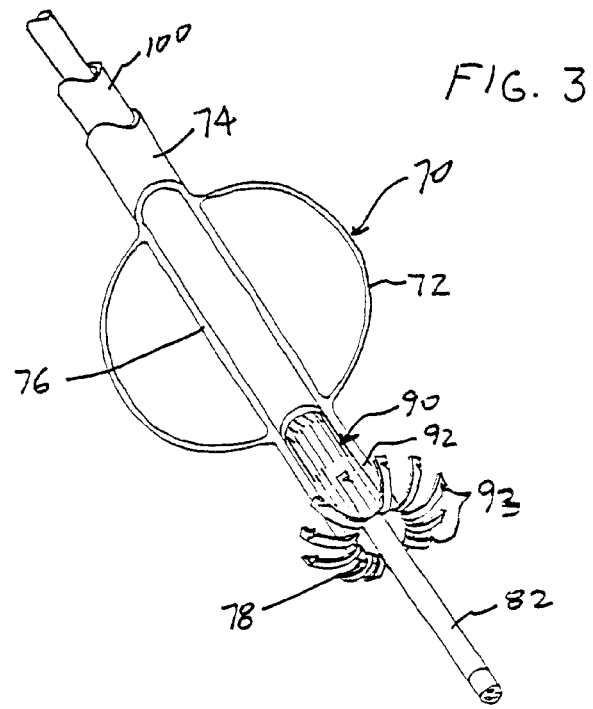
FIG. 3 is a perspective view with portions cut away of the device of FIG. 2 illustrating partial deployment of a fastener in accordance with the present invention.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The fundus 46 of the greater curvature 44 forms the superior portion of the stomach 43, and traps gas and air bubbles for burping. The esophageal tract 41 enters the stomach 43 at an esophageal orifice 58 below the superior portion of the fundus 46, forming a cardiac notch 47 and an acute angle with respect to the fundus 46 known as the Angle of His 57. The lower esophageal sphincter (LES) 48 is a discriminating sphincter able to distinguish between burping gas, liquids, and solids, and works in conjunction with the fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 48 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

FIG. 2 shows a device 60 embodying the present invention. As will be seen hereinafter, the device 60 permits transesophageal gastric reduction for treating severe obesity. The device 60 generally includes an expandable structure 70 and an evacuator 80. Shown further in FIG. 2 is a fastener 90 which the device 60 delivers to maintain a formed gastric reduction pouch.

The expandable structure 70, in accordance with this embodiment, takes the form of an inflatable ring-shaped balloon 72 which is integrally formed on and carried by an outer catheter 74. The ring-shaped balloon 72 and catheter 74 define an axial passageway 76. The balloon may be a compliant balloon formed of latex or polyurethane, for example. It may alternatively be a non-compliant balloon formed of polyethylene. A non-compliant balloon may be preferred as it maintains a fixed shape and size once totally inflated rendering the size of the balloon is rendered predictable.

The evacuator 80, in accordance with this embodiment, comprises an endoscope 82 which includes a light source 84, a viewer 86, and a working channel 88. Endo scopes of this type are well known in the art. The working channel 88 is employed for evacuating the stomach once the device 60 is in place within the stomach and the balloon 72 has been inflated. This will become more apparent subsequently.

As will be noted in FIG. 2, the evacuator 80 extends through the expandable structure 70. More specifically, the endoscope 82 may be advanced through the axial passageway 76 to terminate distal to the expandable structure 70 to facilitate the evacuation of the stomach. The fastener 90 may be carried by the endo scope 82 and also advanced through the axial passageway 76 along the endoscope 82 by a tubular pusher 100.

Figure 4:
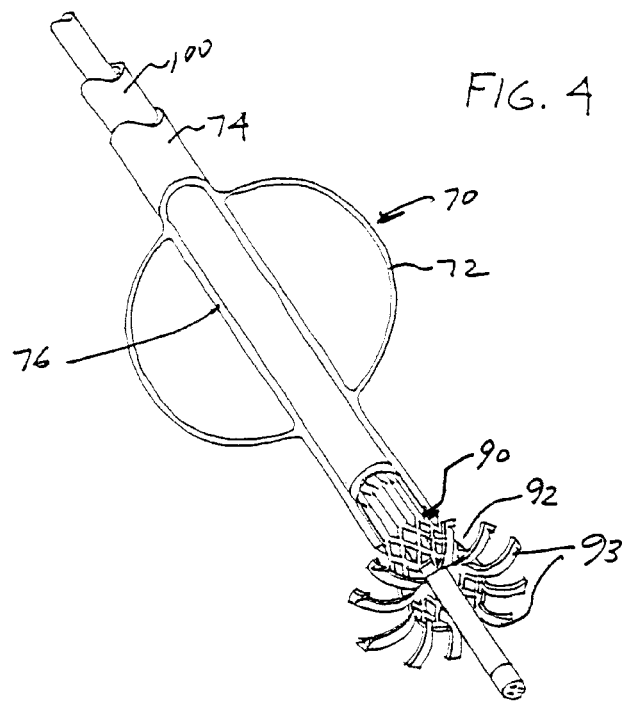
FIG. 4 is a perspective view with portions cut away of the device of FIG. 2 with the fastener in a further stage of deployment.

The fastener 90 is preferably formed of a shape memory material such as Nitinol or a shape memory plastic, for example, so as to be self-deploying when advanced past the distal end 78 of the catheter 74. It alternatively may be formed of stainless steel but would then require forced expansion as, for example, a balloon as is well known in the art. FIG. 3 illustrates the fastener 90 during an initial stage of its deployment. The fastener 90 prior to its deployment takes the form of a cylindrically shaped member 92 having opposed ends from which first and second sets of tissue engaging arms radially extend after deployment. As will be noted in FIG. 3, a first set of tissue engaging arms 93 are radially extending from the cylindrical member 92 as the fastener 90 is advanced by the catheter 100 past the distal end 78 of the catheter 74. Upon further displacement of the fastener 90 as illustrated in FIG. 4, the cylindrical center portion of the cylindrical member 92 is exposed. This forms a channel through which ingested food may pass out of the gastric reduction pouch after it is formed and maintained by the fastener 90.

Figure 5:
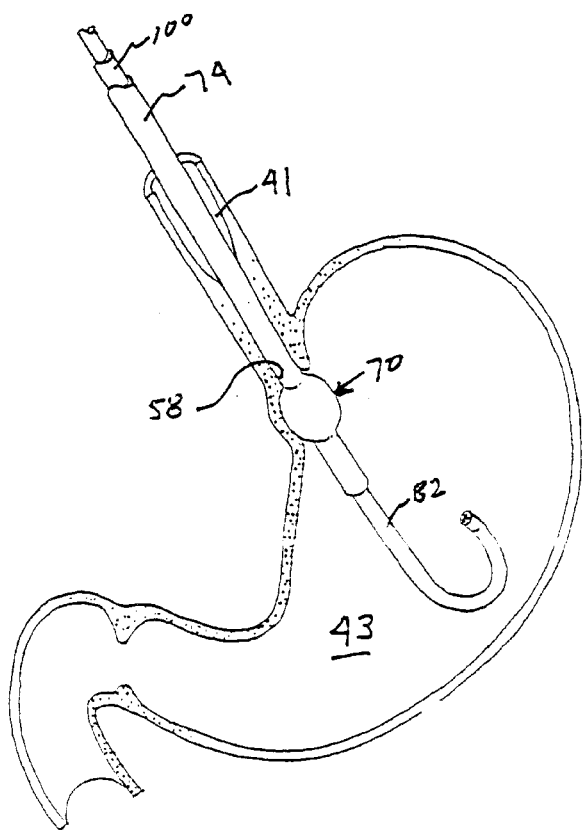
FIG. 5 is a cross-sectional view of an esophagus and stomach with a device embodying the present invention in an initial stage of gastric reduction therapy in accordance with the present invention.

Referring now to FIG. 5, it illustrates an initial stage of forming the gastric reduction pouch in accordance with the present invention. Here it will be seen that the expandable structure 70 has been advanced through the esophagus 41 on the catheter 74 so that it is placed in the stomach immediately adjacent and distal to the esophageal orifice 58. After the expandable member is positioned adjacent the esophageal orifice 58, the endo scope 82 is advanced through the axial passageway of the catheter 74 and expandable structure 70 until it is distal to the catheter 74 and expandable structure 70 within the stomach 43.

Figure 6:
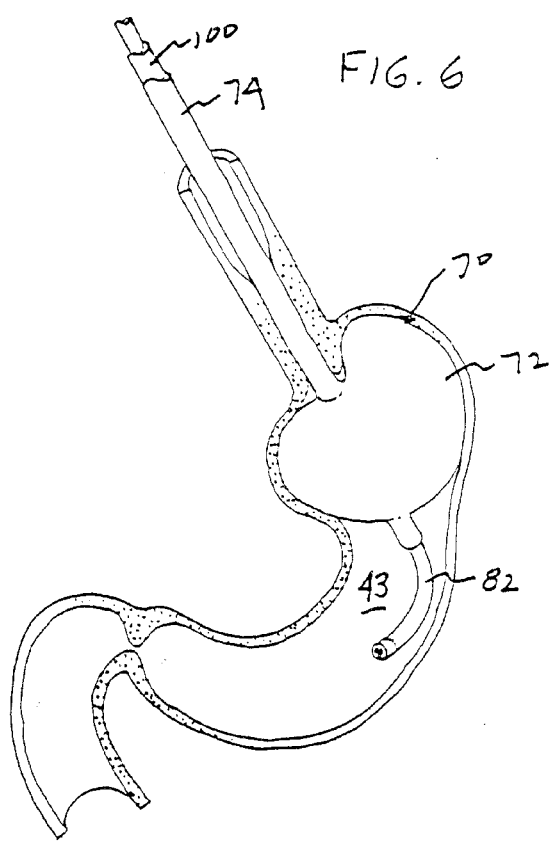
FIG. 6 is a cross-sectional view similar to FIG. 5 of the device in a further stage of the therapy.

After the expandable structure 70 and endo scope 82 are placed in the stomach 43 as illustrated in FIG. 5, the expandable structure 70 is expanded to define the size and shape of the gastric reduction pouch to be formed. In accordance with this preferred embodiment, the expandable structure 70 comprises a balloon 72 which may be inflated as illustrated in FIG. 6. Here it may be seen that the balloon 72 has been inflated and occupies a fraction or portion of the stomach 43. The balloon 72 may be inflated through a lumen (not shown) in the catheter 74 in a manner well known in the art.

After the balloon 72 has been expanded to its desired size, the stomach 43 is evacuated through the working channel of the endoscope 82 to cause the stomach to be drawn around the balloon 72.

Once the stomach tissue has been drawn around the balloon 72, the fastener 90 is then advanced down the endoscope 82 by the pusher 100 for deploying the fastener 90. As shown in FIG. 7, the fastener 90 is partially deployed with the first set of tissue engaging arms 93 radially extending from the cylindrical body 92 of the fastener 90. Upon further advancement of the fastener 90 as illustrated in FIG. 8, the second set of tissue engaging arms 95 are released from the catheter 74 to radially extend from the cylindrical body 92 of the fastener 90.

The shape memory of the fastener 90 may be used to advantage by which the opposed sets of radially extending tissue engaging arms 93 and 95 together with the drawing of the stomach around the balloon 72 inwardly folds the outer surfaces of the stomach 43 to cause contact between adjacent outer surfaces of the stomach about the cylindrical body 92 of the fastener 90. The outer surface of the stomach comprises serosa tissue which develops a bond after contacting like tissue within a short period of time. This bond between the outer surfaces of the contacting stomach tissue will assist the fastener 90 in maintaining the gastric reduction pouch thus formed.

Figure 9:
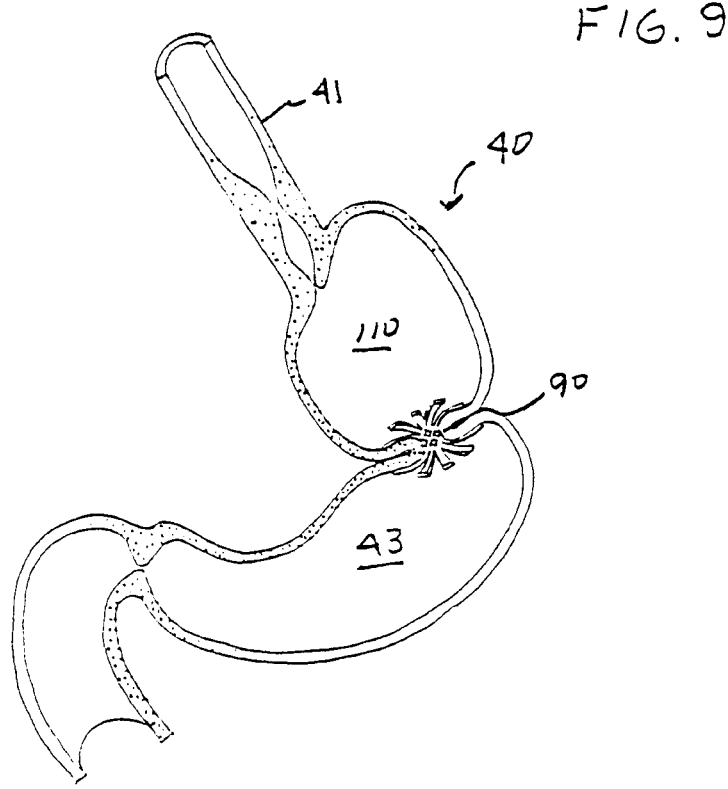
FIG. 9 is a cross-sectional view similar to FIG. 5 after completion of the therapy and removal of the device embodying the present invention.

Once the fastener 90 has been fully deployed as illustrated in FIG. 8, the assembly and device 60 is removed from the stomach. This may be achieved by first drawing the pusher 100 out of the catheter 74. Then, the balloon 72 may be deflated permitting the balloon 72 and catheter 74 to be withdrawn from the stomach on the endoscope 82. Lastly, the endoscope 82 may be withdrawn through the fastener 90, through the gastric reduction pouch formed by the assembly and device 60, and the esophagus 41. This leaves the esophageal-gastro-intestinal tract 40 in a condition as illustrated in FIG. 9. Here it may be seen that the gastric reduction pouch 110 has been formed between the esophagus 41 and the remaining stomach 43. The fastener 90 may remain in place to maintain the gastric reduction pouch 110. The gastric reduction pouch 110 presents a smaller volume to accommodate ingested food thus providing the patient with an earlier sense of being full and a longer time of feeling full.

As will be noted from the foregoing, the process of forming the gastric reduction pouch 110 with the device 60 embodying the present invention has been performed in a transesophageal manner without the need of any surgical incisions. Hence, the therapy contemplated herein is much less invasive than previous therapies for providing gastric reduction therapy. All of the advantages of gastric reduction therapy are available while substantially reducing the risks attendant to general surgery.

While particular embodiments of the present invention have been shown and described, modifications may be made, and it is therefore intended in the appended claims to cover all such changes and modifications which fall within the true spirit and scope of the invention.

What is claimed is:

1. A method of forming a gastric reduction pouch comprising the steps of:

introducing a device into a stomach, the device having an expandable structure movable between a collapsed position and an expanded position, means for evacuating the stomach to deflate the stomach around the expandable structure when the expandable structure is expanded to form a gastric reduction pouch, the introducing step also being carried out with the evacuating means extending through the expandable structure, wherein the fastener is carried on the evacuating means, and wherein the device also includes a pusher that pushes the fastener through the expandable member;

expanding the expandable structure inside the stomach;

evacuating the stomach using the evacuating means to deflate the stomach around the expandable structure while the expandable structure is expanded;

fastening an annular fold of the stomach adjacent a distal end of the expanded expandable structure to maintain the gastric reduction pouch using a fastener, the fastener being positioned distal to the expandable structure when the fastener is initially secured to the annular fold of the stomach; and removing the expandable structure from the stomach.

2. The method of claim 1 wherein:
the introducing step is carried out with the expandable structure being placed in the stomach immediately adjacent and distal to an esophageal orifice associated with the stomach.

3. The method of claim 1 wherein:
the introducing step is carried out with the expandable structure being a balloon.

4. The method of claim 1 wherein:
the evacuating step is carried out with the evacuating means extending distally from the expandable structure and terminating within the stomach.

5. The method of claim 1 wherein:
the fastening step is carried out with the fastener inwardly folding stomach tissue to fasten serosa tissue to serosa tissue of the stomach.

6. The method of claim 1 wherein:
the fastening step is carried out with the fastener being a cylindrically shaped member having opposed ends and tissue engaging arms radially extending from each of the opposed ends.

7. A method of forming a gastric reduction pouch comprising the steps of:
introducing a device into a stomach, the device having an expandable structure movable between a collapsed position and an expanded position, means for evacuating the stomach to deflate the stomach around the expandable structure when the expandable structure is expanded to form a gastric reduction pouch;
expanding the expandable structure inside the stomach;
evacuating the stomach using the evacuating means to deflate the stomach around the expandable structure while the expandable structure is expanded, the evacuating step being carried out with the evacuating means including an endoscope that extends through the expandable structure;
fastening an annular fold of the stomach adjacent a distal end of the expanded expandable structure to maintain the gastric reduction pouch using a fastener, the fastener being positioned distal to the expandable structure when the fastener is initially secured to the annular fold of the stomach; and
removing the expandable structure from the stomach.

8. The method of claim 7 wherein:
the introducing step is carried out with the expandable structure being placed in the stomach immediately adjacent and distal to an esophageal orifice associated with the stomach.

9. The method of claim 7 wherein:
the introducing step is carried out with the expandable structure being a balloon.

10. The method of claim 7 wherein:
the evacuating step is carried out with the evacuating means extending distally from the expandable structure and terminating within the stomach.

11. The method of claim 7 wherein:
the introducing step is carried out with the evacuating means extending through the expandable structure, wherein the fastener is carried on the evacuating means, and wherein the device also includes a pusher that pushes the fastener through the expandable member.

12. The method of claim 7 wherein:
the fastening step is carried out with the fastener inwardly folding stomach tissue to fasten serosa tissue to serosa tissue of the stomach.

13. The method of claim 7 wherein:
the fastening step is carried out with the fastener being a cylindrically shaped member having opposed ends and tissue engaging arms radially extending from each of the opposed ends.

* * * * *